(12) United States Patent
Blanco et al.

(10) Patent No.: US 10,058,246 B2
(45) Date of Patent: Aug. 28, 2018

(54) SYSTEM AND METHOD FOR REJECTING AFOCAL LIGHT COLLECTED FROM AN IN VIVO HUMAN RETINA

(71) Applicant: NeuroVision Imaging LLC, Sacramento, CA (US)

(72) Inventors: Austin Blanco, Sacramento, CA (US); Steven Verdooner, Sacramento, CA (US); David Biggs, Sacramento, CA (US)

(73) Assignee: NeuroVision Imaging, Inc., Sacramento, CA (US)

( * ) Notice: Subject to any disclaimer, the term of this patent is extended or adjusted under 35 U.S.C. 154(b) by 0 days.

(21) Appl. No.: 14/211,406

(22) Filed: Mar. 14, 2014

(65) Prior Publication Data

US 2016/0206199 A1    Jul. 21, 2016

Related U.S. Application Data

(60) Provisional application No. 61/793,819, filed on Mar. 15, 2013.

(51) Int. Cl.
*A61B 3/14* (2006.01)
*A61B 3/15* (2006.01)
(Continued)

(52) U.S. Cl.
CPC ............ *A61B 3/156* (2013.01); *A61B 3/0008* (2013.01); *A61B 3/0025* (2013.01);
(Continued)

(58) Field of Classification Search
CPC ......... A61B 3/103; A61B 3/02; A61B 3/1015; A61B 3/14; A61B 3/12; A61B 3/156
(Continued)

(56) References Cited

U.S. PATENT DOCUMENTS 4,743,107 A * 5/1988 Aizu et al. .................... 351/221
4,767,204 A * 8/1988 Blaha ............................ 351/214
(Continued)

FOREIGN PATENT DOCUMENTS

DE        19922593 A1    11/1999
DE        10014331 A1    10/2000
(Continued)

OTHER PUBLICATIONS

EPO Search Report for 14770358.1 / PCT/US2014027643, dated Feb. 2, 2017.
(Continued)

*Primary Examiner* — James Greece
(74) *Attorney, Agent, or Firm* — Lucas & Mercanti, LLP; Peter J. Phillips

(57) ABSTRACT

A system and method for rejecting afocal light collected from an in vivo human retina is disclosed. The system may include a detector, a server system being in communication with the detector and a memory system with a rejection of collected afocal light and a disk having an optointerruptor and a motor, which is speed controlled via a non-transitory storage media. The method includes utilizing a series of optical shapes or codes, similar to other structured illumination systems, illuminating the series of optical shapes or codes several times, collecting and processing the series of optical shapes or codes yielding measurements of optical noise and optical signal and subtracting the noise and signal from the final image.

31 Claims, 10 Drawing Sheets

(51) Int. Cl.
*G02B 21/00* (2006.01)
*A61B 3/00* (2006.01)
*A61B 3/10* (2006.01)
*A61B 3/135* (2006.01)

(52) U.S. Cl.
CPC ............ *A61B 3/1025* (2013.01); *A61B 3/135* (2013.01); *G02B 21/0004* (2013.01); *G02B 21/0012* (2013.01); *G02B 21/0044* (2013.01)

(58) Field of Classification Search
USPC .................. 351/200, 205, 206, 207, 246
See application file for complete search history.

(56) References Cited

U.S. PATENT DOCUMENTS

| | | | |
|---|---|---|---|
| 5,204,705 A * | 4/1993 | Akiyama et al. ............ | 351/221 |
| 5,532,771 A | 7/1996 | Johnson | |
| 6,320,185 B1 | 11/2001 | Matsuo | |
| 6,341,035 B1 | 1/2002 | Miura | |
| 6,379,005 B1 | 4/2002 | Williams | |
| 2003/0231285 A1 | 12/2003 | Ferguson | |
| 2004/0032650 A1* | 2/2004 | Lauer .................. | G02B 21/004 |
| | | | 359/385 |
| 2006/0238711 A1* | 10/2006 | Kitajima ................ | A61B 3/135 |
| | | | 351/214 |
| 2007/0146869 A1* | 6/2007 | Lauer .................... | G02B 5/005 |
| | | | 359/368 |
| 2007/0236661 A1* | 10/2007 | Fukuma et al. ............ | 351/205 |
| 2008/0284981 A1* | 11/2008 | Fercher ........................ | 351/221 |
| 2011/0234977 A1 | 9/2011 | Verdooner | |
| 2012/0081535 A1 | 4/2012 | Hayashi | |
| 2013/0057828 A1 | 3/2013 | De Smet | |
| 2014/0092362 A1* | 4/2014 | Narayanaswamy et al. ........ | |
| | | | 351/221 |
| 2015/0168702 A1* | 6/2015 | Harris ................... | G02B 21/08 |
| | | | 850/30 |

FOREIGN PATENT DOCUMENTS

| | | |
|---|---|---|
| DE | 102007047460 A1 | 4/2009 |
| EP | 2520965 A1 | 11/2012 |
| JP | H05508235 | 11/1993 |
| JP | H10-048530 | 2/1998 |
| JP | H11-326770 | 11/1999 |
| JP | 2001521422 T | 11/2001 |
| JP | 2003043363 | 2/2003 |
| JP | 2004-514920 | 5/2004 |
| JP | 2007117714 | 5/2007 |
| JP | 2008046362 | 2/2008 |
| JP | 2008129172 A | 6/2008 |
| JP | 2012-078408 | 4/2012 |
| WO | 9846122 A1 | 10/1998 |
| WO | 0184209 A2 | 11/2001 |
| WO | WO 2014005195 A2 * | 1/2014 ............ G02B 21/08 |

OTHER PUBLICATIONS

Japanese Office Action for Patent Application No. 2016-502502, dated Jan. 9, 2018.
English Translation of Japanese Office Action for Patent Application No. 2016-502502, dated Jan. 9, 2018.

* cited by examiner

SYSTEM AND METHOD FOR REJECTING AFOCAL LIGHT COLLECTED FROM AN IN VIVO HUMAN RETINA

This application claims priority to U.S. Provisional Application 61/793,819 filed on Mar. 15, 2013, the entire disclosure of which is incorporated by reference.

BACKGROUND OF THE INVENTION

Field of the Invention

The present invention is a system and method for imaging. More specifically, the present invention is a system and method for rejecting afocal light collected from an in vivo human retina.

Description of the Related Art

Current imaging modalities for the human retina rely on one of two distinct methods: flood Illumination, wherein a standard broadband wide field illumination source is delivered into the retina, and then all return light is imaged, or via a confocal laser scanning ophthalmoscope, wherein a point of light is delivered into the retina via a combination of polygonal mirrors and a galvanometric motor and mirrors, and the return signal from this point is simultaneously imaged to a photomultiplier tube, PMT detector, avalanche photodiode or APD detector. This type of confocal makes use of the confocal pinhole effect, and may include a pinhole of changing diameter, to allow the operator of the system control over the confocality of the image and corresponding rejection of afocal light.

Both systems have several limitations. The flood illumination fundus camera has the benefit of lower cost, as the device relies on a fluorescent exciting gas-arc, white light, or LED excitation or delivery source, but because this system delivers illumination in both a focal plane and out of focus planes, numerous artifacts and reflections are present in the image, and are visualized as sources of noise and/or reflection areas, where the image is blocked entirely and thereby unusable in those regions. In addition to the artifacts produced, the afocal haze present in the return image limits the optical system's sensitivity to small objects. While the resolution of the system is not limited to haze, the minimum resolvable object size is limited by the minimally detectable background to signal level. Because haze is a source of background, this haze may overcome small signals produced by diffraction limited points of signal, thereby rendering the effective resolution limit of the system lower than the optimal resolution limit of the optical path as expressed by The Rayleigh Criterion.

A confocal laser scanning ophthalmoscope or CLSO overcomes several of the limitations found in a flood illumination system, but at a relatively great increase in cost and component complexity. First, the CLSO relies upon a pinhole to reject out of focus light. This rejection overcomes the resolution and haze problem found in the flood illumination system. In addition, because a single point of light is simultaneously delivered and sampled on the system, any errors in the lens assembly of the specimen (i.e., cornea of the person being imaged) are mitigated to those errors which directly interact with the image point being collected. This reduces or eliminates the artifacts found in the flood illumination system, providing a greater useful area for analysis in the image on a typical patient. While these advantages do result in substantial effective resolution improvements and image quality improvements, they come at a relatively great cost and complexity increase. In order to produce a scanned image, several high cost items must be utilized. First, the light delivered into the subject must be coherent. The only system capable of currently delivering coherent light is a gas laser or a diode laser. Lasers with the required performance specifications utilized on a CLSO have a high cost for a single wavelength, and as most operators and owners want several colors in the image, multiple lasers must be coupled to the system. In addition, the descanning of any image must be accomplished through a proprietary signal processing system. This system is a custom product that measures the return signal from any scanned point, and builds-up a raster image, which is then presented as a three dimensional structure to the user (i.e., having X, Y and Intensity axes expressed as X,Y and pixel brightness). In addition, should one of the beam steering systems fail, the potential for damage to the subject exists. This then requires several safety features to be added to the instrument, which, should a beam steering unit fail, will cut the laser power before damage may occur to the subject being imaged.

BRIEF SUMMARY OF THE INVENTION

The present invention is a system and method for imaging. More specifically, the present invention is a system and method for rejecting afocal light collected from an in vivo human retina.

The system and method for rejecting afocal light collected from an in vivo human retina utilizes an amalgamation of these two systems, while simultaneously coupling already available technology utilized in the field of confocal microscopy and emerging technologies in coded optical systems. To achieve confocality, a pinhole must be utilized as we've described above, to eliminate haze from the return image. Existing systems and methods rely on the pinhole utilizing a fixed single point detector, such as a photodiode or photomultiplier, sitting behind a pinhole fixed in space. The image is scanned by moving the effective detection point across a field of the retina. The system and method instead fixes the illumination and return paths, and moves the pinhole over the surface of the detector and may be utilized to interact with the delivery light as well. This is effectively the same solution employed on spinning disk confocals utilized in modem fluorescent microscopy, such as the Yokagawa CSU XI, which relies on a Nipkow Disk including microarray lens technology, to maximize the collection of all focal light through the disk. While utilizing the basic premise of a scanning pinhole array, as is utilized on the systems for microscopy, the system provides several new and novel improvements upon current technology. Firstly, all current spinning disk systems are only utilized on microscopes, have effective pinhole sizes which are matched to high numerical aperture oil immersion lenses for microscopy, and are of a size and configuration as to provide stability for very high magnification imaging (i.e. heavy and large).

It is an object of the present invention to provide a system and method for rejecting afocal light collected from an in vivo human retina that sacrifices weight for the advantages of portability, while sacrificing rigidity knowing that small vibrations won't affect the lower magnification images collected on our device.

It is an object of the present invention to provide a system and method for rejecting afocal light collected from an in vivo human retina that includes a reflective side of a disk.

It is an object of the present invention to provide a system and method for rejecting afocal light collected from an in vivo human retina that utilizes an angled disk wherein one side of the disk is coated with a highly reflective material such as aluminum, or is constructed of a highly reflective material, or is manufactured lithographically with a reflecting face. This coating will allow for traditional flood illumination delivery of input light, but will include the focal specificity found on a scanning confocal, as a pinhole array will reject afocal light from the return image.

It is an object of the present invention to provide a system and method for rejecting afocal light collected from an in vivo human retina that does not utilize a pinhole but instead provides a slit, series of cuts or shapes on the disk, to make a compromise between focal specificity and overall collection efficiency.

It is an object of the present invention to provide a system and method for rejecting afocal light collected from an in vivo human retina that provides for the owner or operator of the device to exchange spinning disks. Using the system and method the operator may choose between numerous focal specificities, allowing for greater control over the image quality.

It is an object of the present invention to provide a system and method for rejecting afocal light collected from an in vivo human retina that includes a time-sequenced series of spaced similarly oriented slits to collect a scanned image. While slit scanning instruments exist, these systems have a linear detector and move the scanning slit across the subject's retina, or fix the aperture and use prisms to move the light path to the aperture. The proposed system would move the aperture, leaving other optical components fixed.

It is an object of the present invention to provide a system and method for rejecting afocal light collected from an in vivo human retina that includes a moving slit, which may be replaced with different sized slit widths, mounted in a wheel. The wheel would include a cut or a mark or other index on its side, which would allow for an optical interrupter, or a magnetic sensor, to detect its index position. This then would allow for mode-locked scanning while using a traditional XY array detector, rather than a linear detector.

It is an object of the present invention to provide a system and method for rejecting afocal light collected from an in vivo human retina that utilizes a series of optical shapes, or codes, similar to other structured illumination systems, to illuminate the image field several times, which when collected and processed in software such as non-transitory storage media, yield measurements of both optical noise and signal, allowing the non-transitory storage media to subtract the noise from the final image, and infer greater source resolution via scattering analysis, achieving a similar result as a confocal system but with an increase in spatial resolution.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
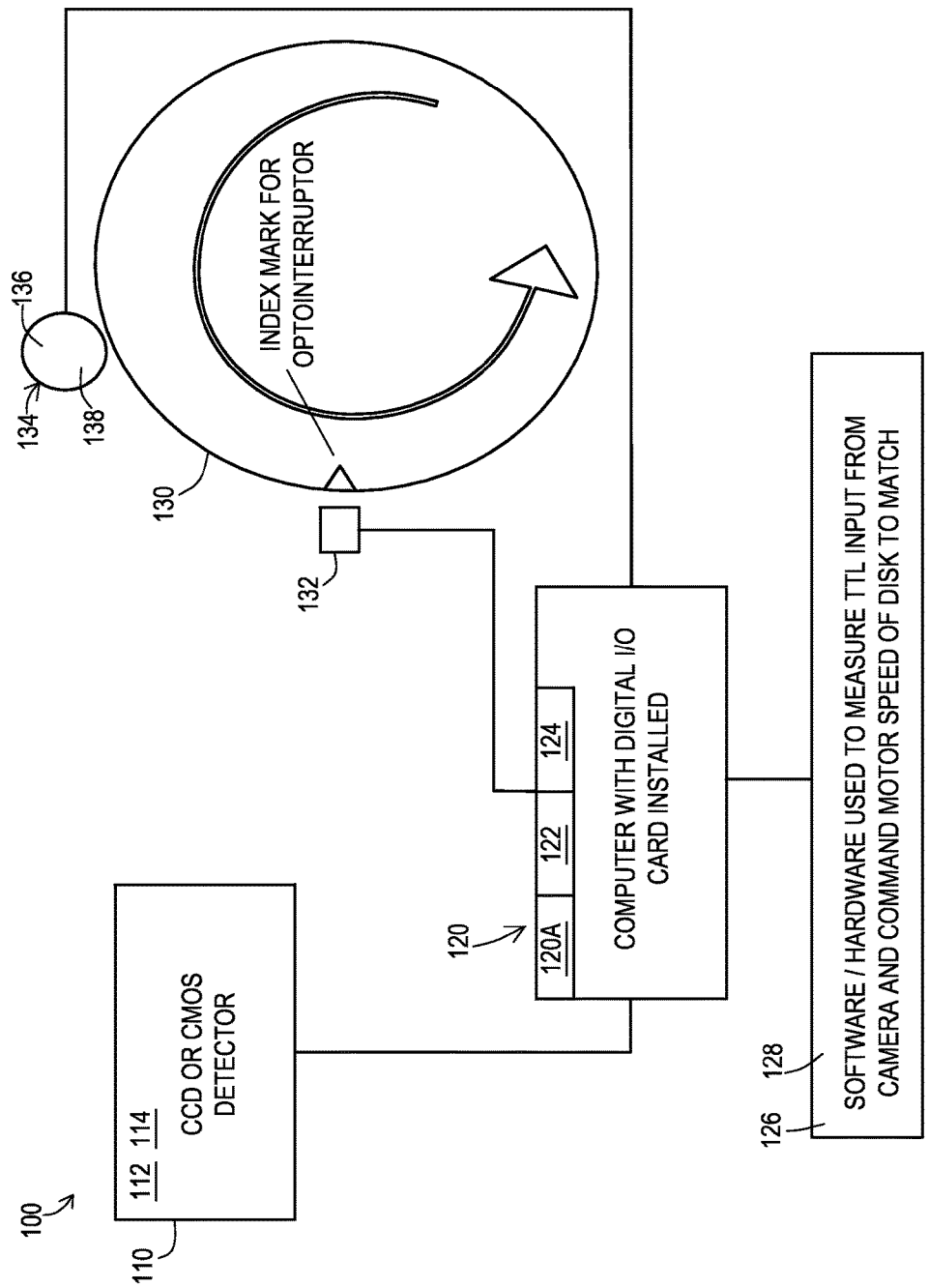
FIG. 1 illustrates a diagram of a system to reject afocal light collected from an in vivo human retina, in accordance with one embodiment of the present invention.

FIG. 1 illustrates a diagram of a system 100 to reject afocal light collected from an in vivo human retina, in accordance with one embodiment of the present invention.

Figure 6:
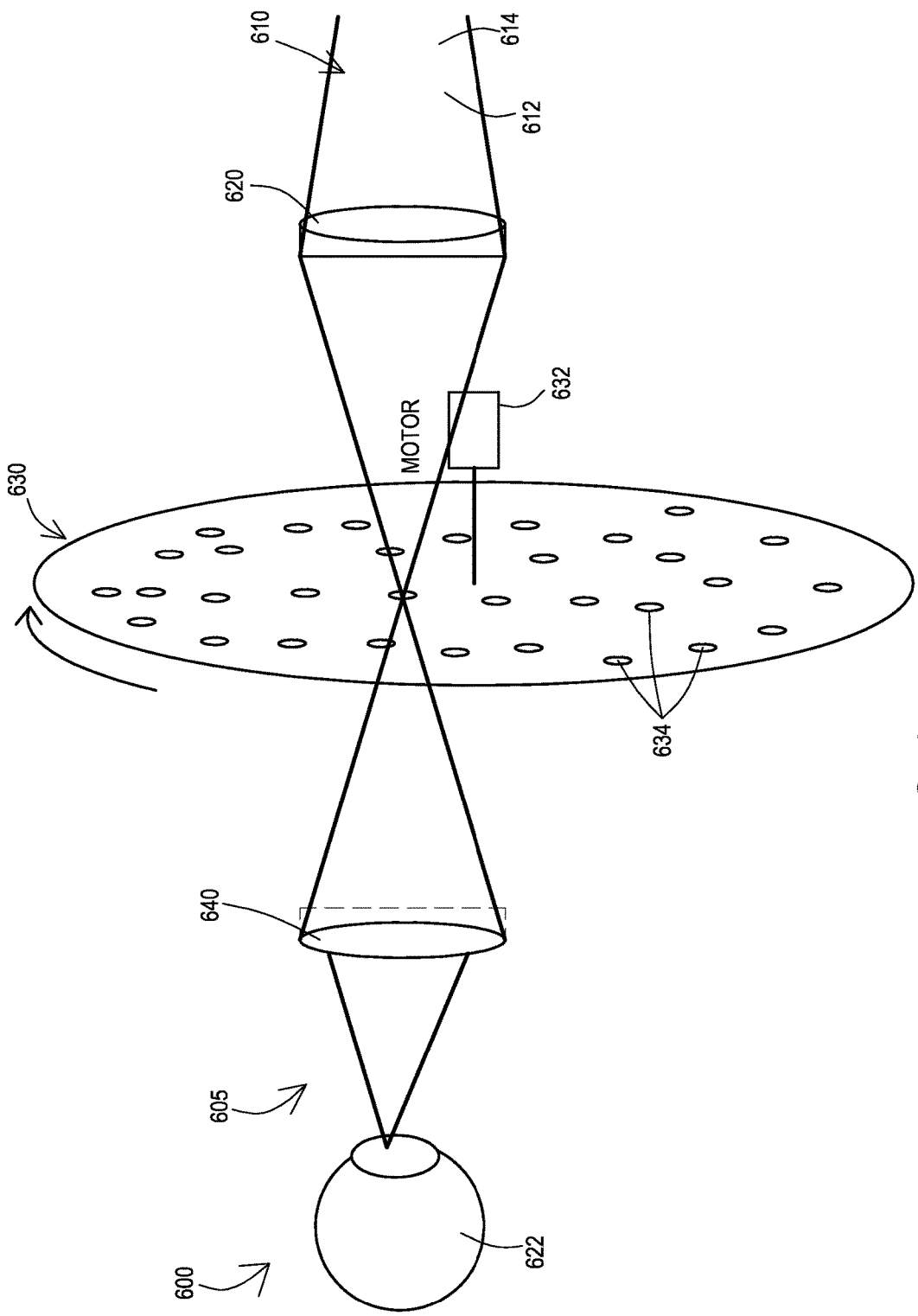
FIG. 6 illustrates an image return path, in accordance with one embodiment of the present invention.

The system 100 may include a detector 110, a computer 120 and a spinning disk 130. The detector 110 may be a charge coupled device or CCD detector 112, a complementary metal oxide semiconductor or CMOS detector 114 or other suitable type of detector. The computer 120 may be in communication with the detector 110 and send an exposure transistor-transistor logic signal from a camera (FIG. 6, 610). The computer 120 may include a server system 122, a memory system 124, a non-transitory storage media 126 and a plurality of computer hardware 128. The computer 120 may include an installed digital input and output card 120A. The spinning disk 130 may have an optointerruptor 132 and a motor 134. The motor 134 may be an axial motor 136 or an offset drive motor 138. The spinning disk 130 may have an index mark for the optointerruptor 132. The non-transitory storage media 126 and the computer hardware 128 may be used to measure total input from the camera (FIG. 6, 610) and command the motor speed of the spinning disk 130. The computer 120 may fire an opto input signal when the index mark is seen. The motor 134 may receive a pulse width modulation or PWM signal from the computer 120 to control direct current or DC motor speed.

Figure 2:
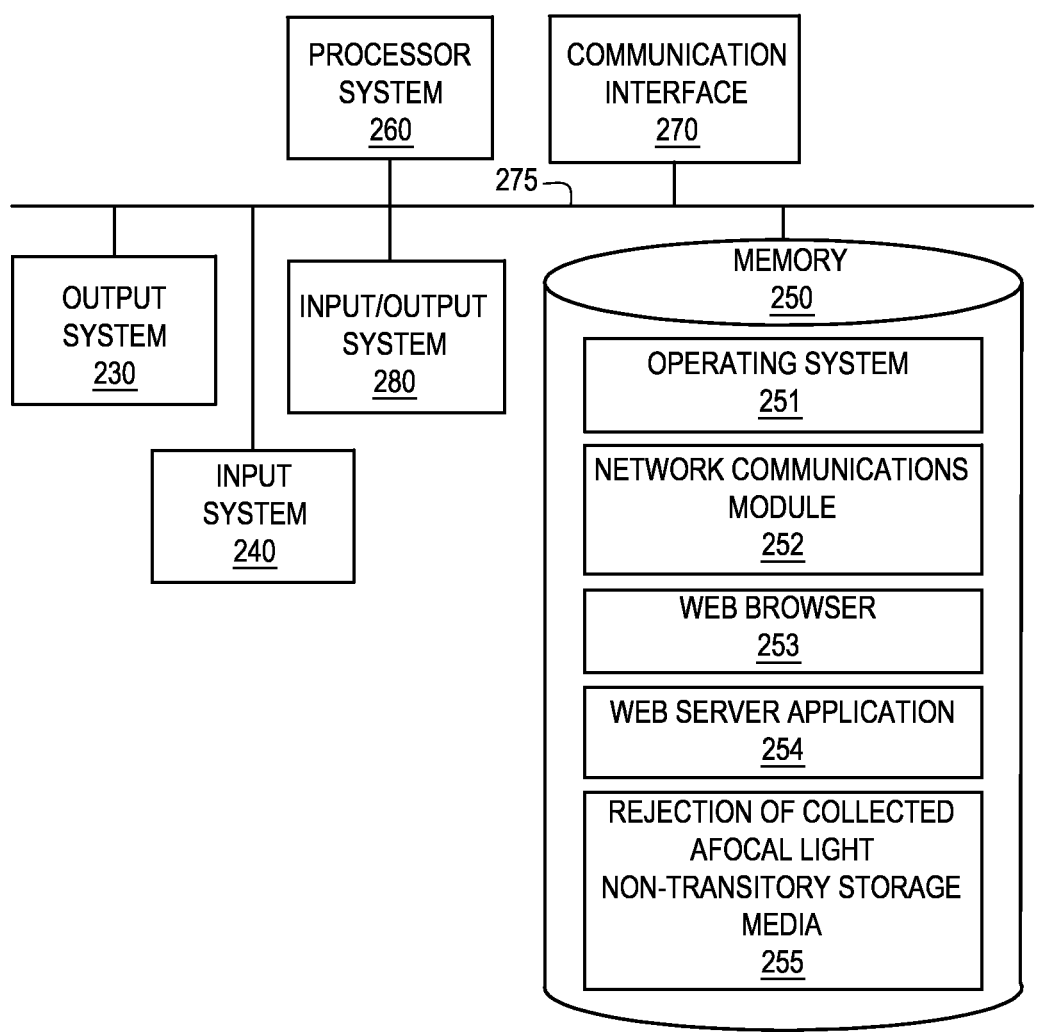
FIG. 2 illustrates a block diagram of a server system, in accordance with one embodiment of the present invention.

FIG. 2 illustrates a block diagram of a server system 200, in accordance with one embodiment of the present invention.

The server system 200 may include an output system 230, an input system 240, a memory system 250, which may store an operating system 251, a communications module 252, a web browser module 253, a web server application 254 and a rejection of collected afocal light non-transitory storage media 255. The server system 200 may also include a processor system 260, a communications interface 270, a communications system 275 and an input/output system 280. In other embodiments, the server system 200 may include additional components and/or may not include all of the components listed above.

The output system 230 may include any one of, some of, any combination of, or all of a monitor system, a handheld display system, a printer system, a speaker system, a connection or interface system to a sound system, an interface system to one or more peripheral devices and/or a connection and/or interface system to a computer system, an intranet, and/or the Internet.

The input system 240 may include any one of, some of, any combination of, or all of a keyboard system, a mouse system, a track ball system, a track pad system, one or more buttons on a handheld system, a scanner system, a microphone system, a connection to a sound system, and/or a connection and/or an interface system to a computer system, an intranet, and/or the Internet (i.e., IrDA, USB).

The memory system 250 may include any one of, some of, any combination of, or all of a long term storage system, such as a hard drive; a short term storage system, such as a solid state disk; or a removable storage system, or a removable drive and/or a flash memory. The memory system 250 may include one or more machine readable mediums that may store a variety of different types of information. The term machine readable medium may be utilized to refer to any medium capable of carrying information that may be readable by a machine. One example of a machine-readable medium may be a computer-readable medium such as a non-transitory storage media. The memory system 250 may store one or more machine instructions for imaging a patient user's body part. The operating system 251 may control all software or non-transitory storage media and hardware of the system 100. The communications module 252 may enable the server system 304 to communicate on a wired or wireless communications network 312. The web browser module 253 may allow for accessing the device via the network. The web server application 254 may serve a plurality of web pages to client systems that request the web pages, thereby facilitating remote access to acquired data.

The processor system 260 may include any one of, some of, any combination of, or all of multiple parallel processors, a single processor, a system of processors having one or more central processors and/or one or more specialized processors dedicated to specific tasks. The processor system 260 may implement the machine instructions stored in the memory system 250.

In an alternative embodiment, the communication interface 270 may allow the server system 200 to interface with the network 312. In this embodiment, the output system 230 may send communications to the communication interface 270. The communications system 275 communicatively links the output system 230, the input system 240, the memory system 250, the processor system 260 and/or the input/output system 280 to each other. The communications system 275 may include any one of, some of, any combination of, or all of one or more electrical cables, fiber optic cables, and/or sending signals through air or water (i.e., wireless communications). Some examples of sending signals through air are existing 802.11* and 801.* protocols.

The input/output system 280 may include devices that have the dual function as the input and output devices. For example, the input/output system 280 may include one or more touch sensitive screens, which display an image and therefore may be an output device and accept input when the screens may be pressed by a finger or a stylus. The touch sensitive screens may be sensitive to heat and/or pressure. One or more of the input/output devices may be sensitive to a voltage or a current produced by a stylus. The input/output system 280 may be optional and may be utilized in addition to or in place of the output system 230 and/or the input device 240.

Figure 3:
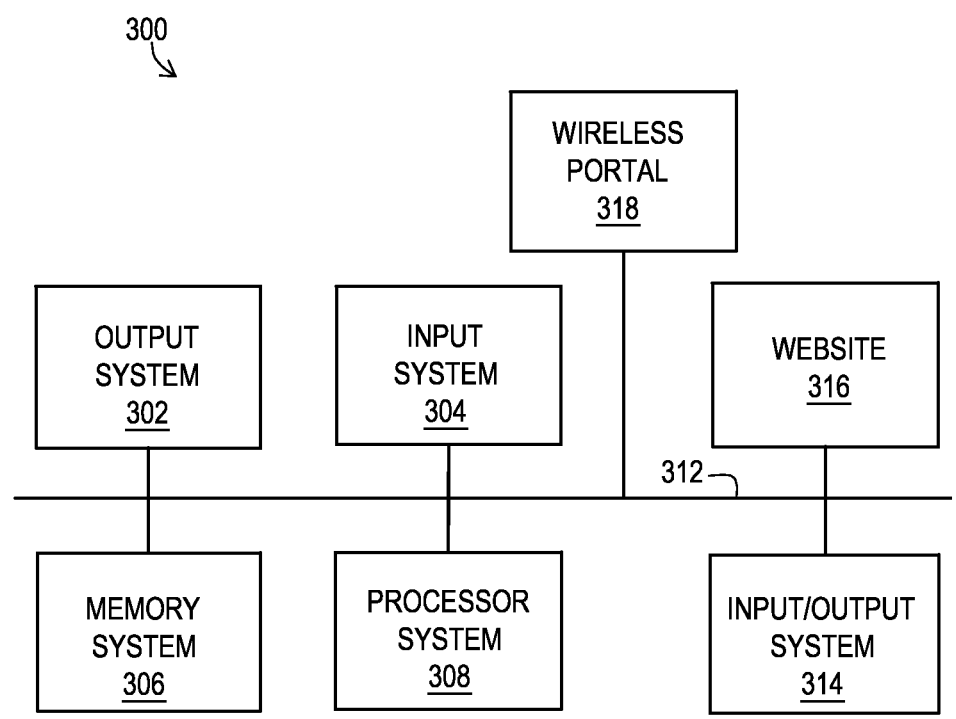
FIG. 3 illustrates a block diagram of a client system, in accordance with one embodiment of the present invention.

FIG. 3 illustrates a block diagram of a client system 300, in accordance with one embodiment of the present invention.

The client system 300 may include an output system 302, an input system 304, a memory system 306, a processor system 308, a communications system 312, an input/output system 314, a website 316 and a wireless portal 318. Other embodiments of the client system 300 may not have all of the components and/or may have other embodiments in addition to or instead of the components listed above.

The client system 300 may be any one of the client systems and/or handheld or mobile wireless device 322, SMARTPHONE® 324 or IPAD® 326 that may be utilized as one of the network devices of FIG. 3. In other embodiments, the client system 300 may include additional components and/or may not include all of the components listed above. The output system 302 may include any one of, some of, any combination of or all of a monitor system, a wireless transmitter, a handheld display system, a printer system, a speaker system, a connection or interface system to a sound system, an interface system to peripheral devices and/or a connection and/or an interface system to a computer system, an intranet, and/or the Internet.

The input system 304 may include any one of, some of, any combination of or all of a keyboard system, a mouse system, a track ball system, a track pad system, one or more buttons on a handheld system, a scanner system, a wireless receiver, a microphone system, a connection to a sound system, and/or a connection and/or an interface system to a computer system, an intranet, and/or the Internet (i.e., Infrared Data Association or IrDA, Universal Serial Bus or USB).

The memory system 306 may include, any one of, some of, any combination of or all of a long-term storage system, such as a hard drive, a short term storage system, such as a random access memory; a removable storage system, such as a floppy drive or a removable drive and/or a flash memory. The memory system 306 may include one or more machine readable mediums that may store a variety of different types of information. The term machine readable medium may be utilized to refer to any medium that may be structurally configured for carrying information in a format that may be readable by a machine. One example of a machine-readable medium may be a computer-readable medium. The memory system 306 may store a rejection of collected afocal light non-transitory storage media (FIG. 2, 255).

The processor system 308 may include any one of, some of, any combination of, or all of multiple parallel processors, a single processor, a system of processors having one or more central processors and/or one or more specialized processors dedicated to specific tasks. The processor system 308 may implement the programs stored in the memory system 306. The communications system 312 may communicatively link the output system 302, the input system 304, the memory system 306, the processor system 308, and/or the input/output system 314 to each other. The communications system 312 may include any one of, some of, any combination of, or all of one or more electrical cables, fiber optic cables, and/or means of sending signals through air or water (i.e., wireless communications). Some examples of means of sending signals through air and/or water may include systems for transmitting electromagnetic waves such as infrared and/or radio waves and/or systems for sending sound waves.

The input/output system 314 may include devices that have the dual function as input and output devices. For example, the input/output system 314 may include one or more touch sensitive screens, which display an image and therefore may be an output device and accept input when the screens may be pressed by a finger or a stylus. The touch sensitive screens may be sensitive to heat, capacitance and/or pressure. One or more of the input/output devices may be sensitive to a voltage or a current produced by a stylus. The input/output system 314 is optional, and may be utilized in addition to or in place of the output system 302 and/or the input device 304.

Figure 4:
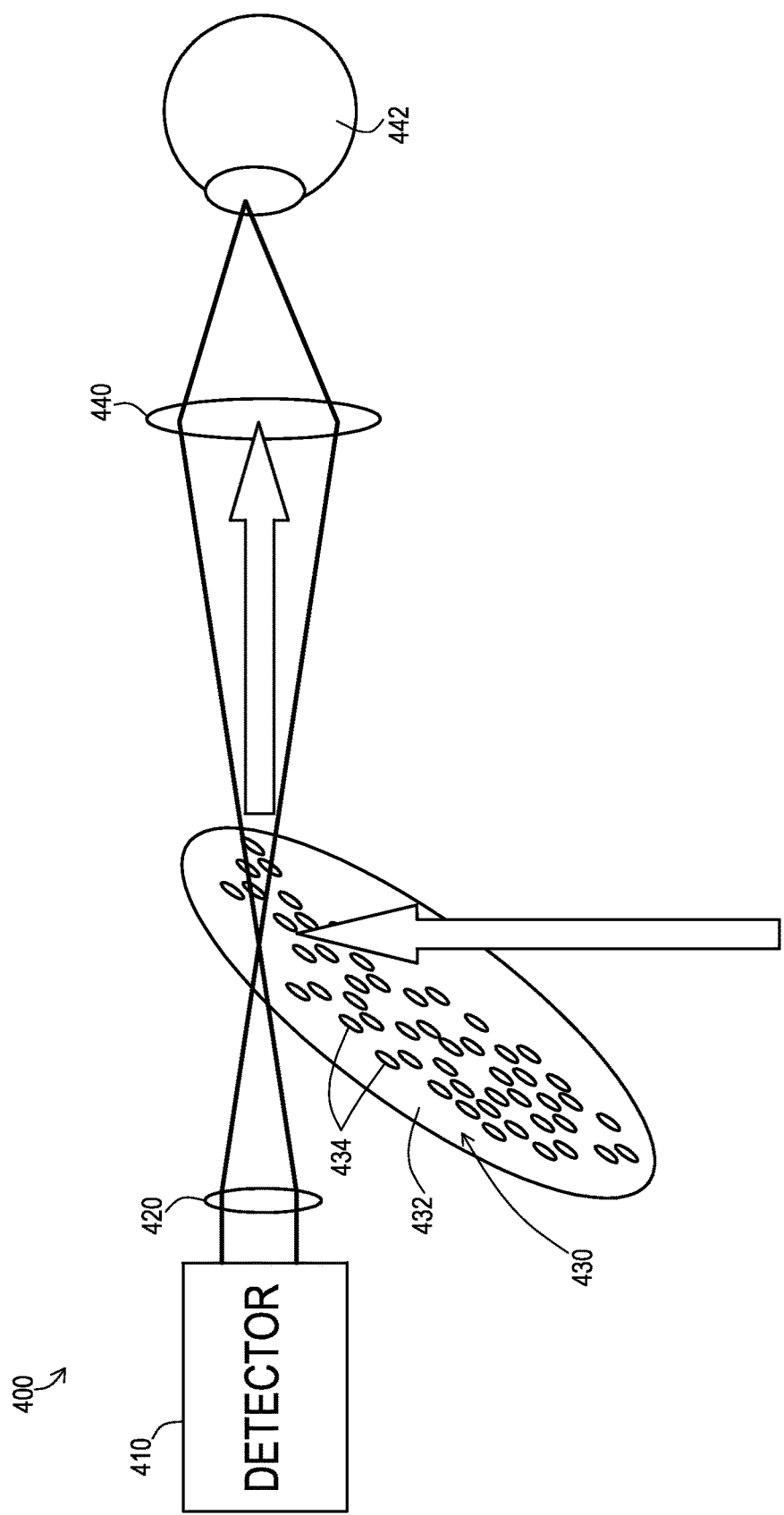
FIG. 4 illustrates an imaging aperture and beam reflector, in accordance with one embodiment of the present invention.

FIG. 4 illustrates an imaging aperture and beam reflector 400, in accordance with one embodiment of the present invention.

The imaging aperture and beam reflector 400 may include a detector 410, a lens 420, a spinning disk 430 and a focusing objective lens 440. The detector 410 may be a charge coupled device or CCD detector 412, a complementary metal oxide semiconductor or CMOS detector 414 or other suitable type of detector. The lens 420 may be positioned in front of the detector 410 to direct light. The spinning disk 430 may have an applied reflected coating 432 that may be tilted to direct polarized white light towards the focusing lens 440. The spinning disk 430 may have a plurality of pin holes 434 that receive and direct light. The focusing lens 440 may focus the directed polarized white light into a patient's eye 442.

Figure 5:
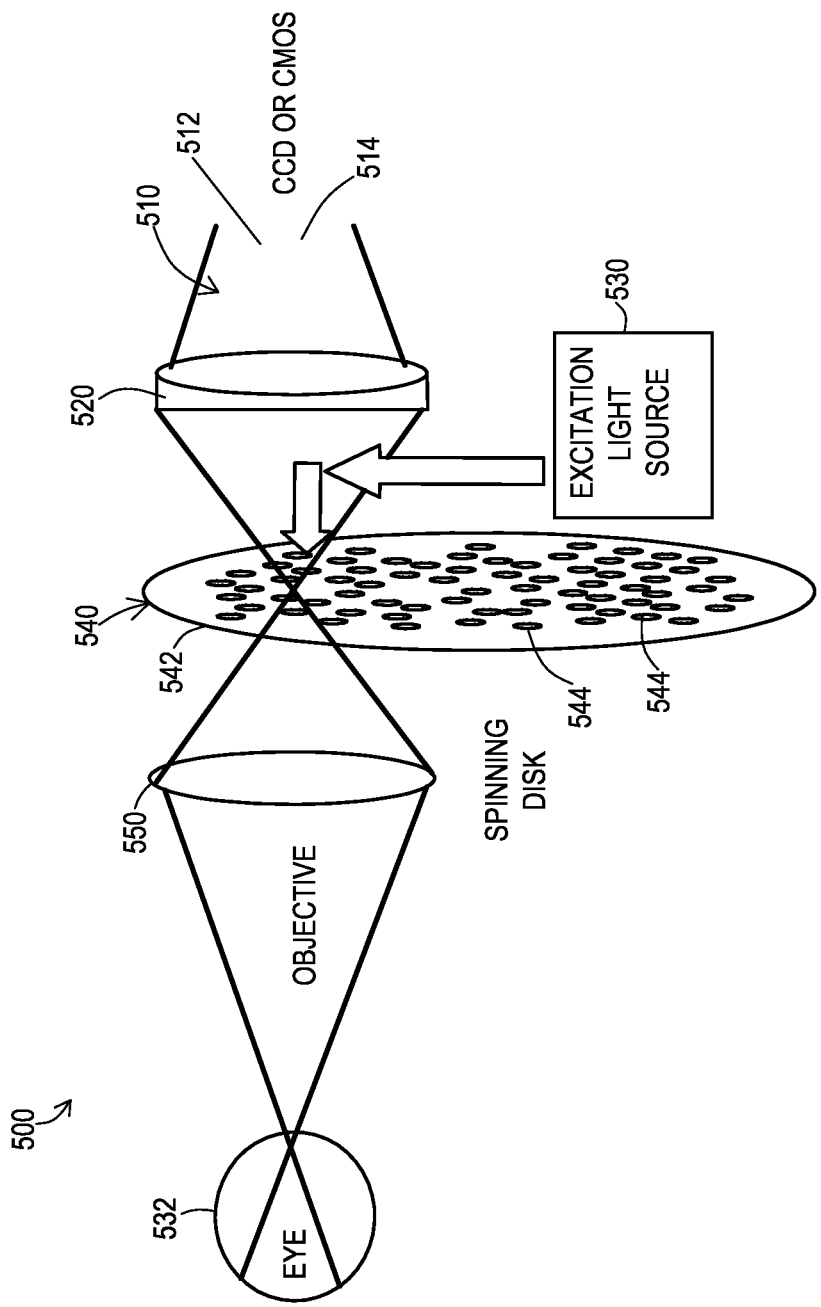
FIG. 5 illustrates a spinning disk light path system, in accordance with one embodiment of the present invention.

FIG. 5 illustrates a spinning disk light path system 500, in accordance with one embodiment of the present invention.

The spinning disk light path system 500 may include a detector 510, a relay lens 520, an excitation light source 530, a spinning disk 540 and an objective lens 550.

The detector 510 may be a charge coupled device or CCD detector 512, a complementary metal oxide semiconductor or CMOS detector 514 or other suitable type of detector. The relay lens 520 may be positioned in front of the detector 510 to direct light. The excitation light source 530 may emit light to be directed to a patent's eye 532. The excitation light source 530 may emit fluorescence light or other suitable light towards the patent user's eye 532. The spinning disk 540 may be positioned in front of the relay lens 520. The spinning disk 540 may be vertically upright at an approximately ninety degrees and may have a plurality of pins holes 544 that receive and reject light. The objective lens 550 may be positioned in front of the spinning disk 530. The objective lens 550 may magnify the emitted light from the spinning disk 540 towards the patent user's eye 532.

FIG. 6 illustrates an image return path 600, in accordance with one embodiment of the present invention. The image return path 600 illustrated in FIG. 6 is for a spinning disk confocal system 605.

The image return path 600 may include a camera 610, an image entry lens 620, a spinning disk 630 and an objective lens 640.

The camera 610 may be a conventional fundus camera 612 or an optical coherence tomography instrument 614. The image reentry lens 620 may be positioned in front of the camera 610 to relay an image of a patent user's eye 622. The spinning disk 630 may have a motor 632 to spin the spinning disk 630. The spinning disk 630 may be vertically upright at an approximately ninety degrees to reject afocal light as it travels towards the camera 610. The spinning disk 630 may have a plurality of pin holes 634 that receive and redirect the image of the patent user's eye 622. The objective lens 640 may be positioned in front of the spinning disk 630. The objective lens 640 may magnify the image of the patent user's eye 622 towards the spinning disk 630.

Figure 7:
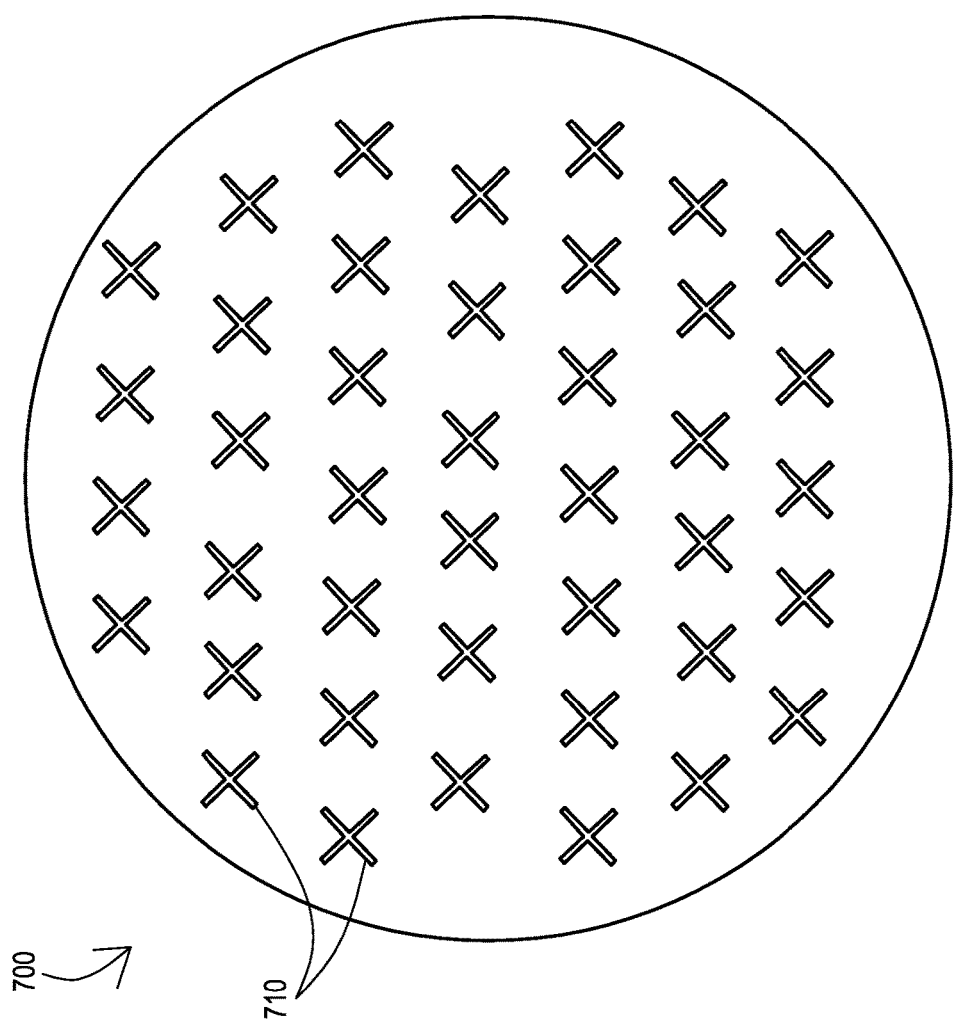
FIG. 7 illustrates a first spinning disk pattern, in accordance with one embodiment of the present invention.

FIG. 7 illustrates a first spinning disk pattern 700, in accordance with one embodiment of the present invention.

The first spinning disk pattern 700 may include a plurality of cross-shaped slits 710 disposed on the first spinning disk pattern 700.

Figure 8:
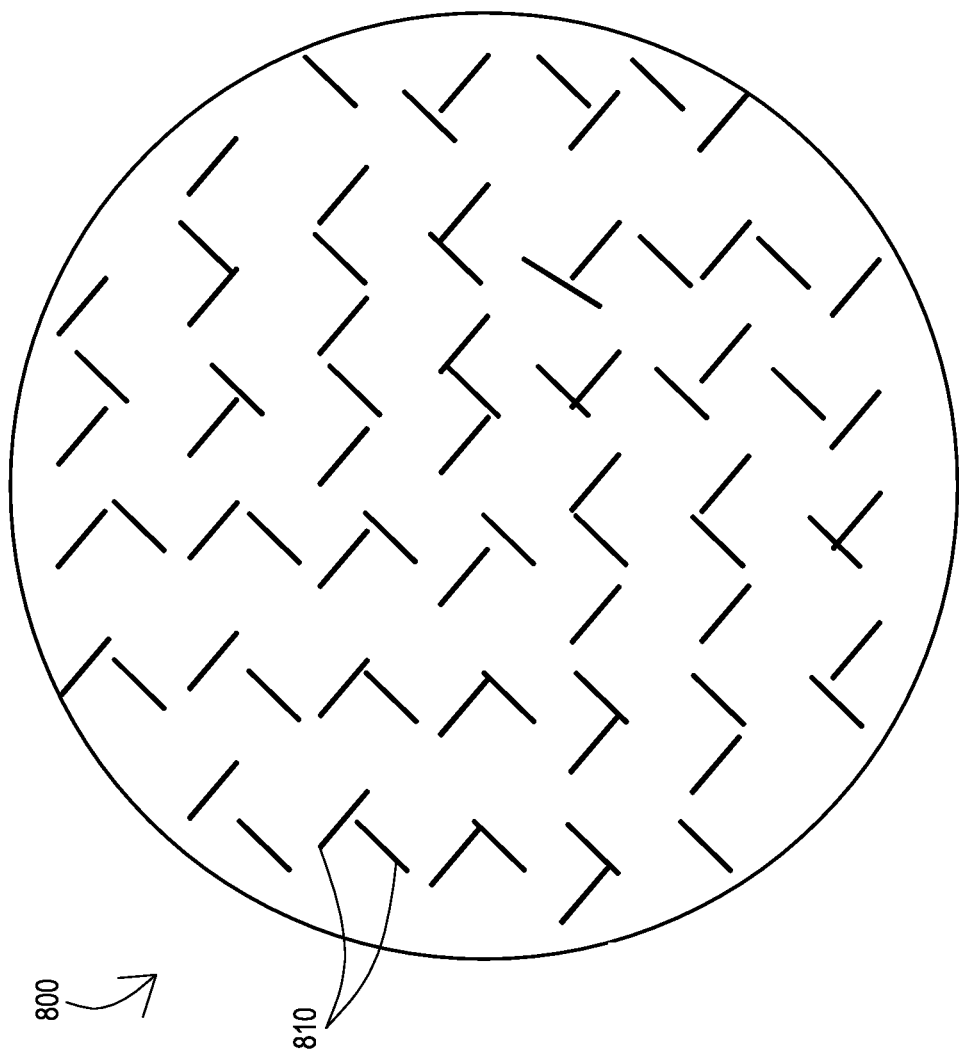
FIG. 8 illustrates a second spinning disk pattern, in accordance with one embodiment of the present invention.

FIG. 8 illustrates a second spinning disk pattern 800, in accordance with one embodiment of the present invention.

The second spinning disk pattern 800 may include a plurality of perpendicular slits 810 disposed on the second spinning disk pattern 800.

Figure 9:
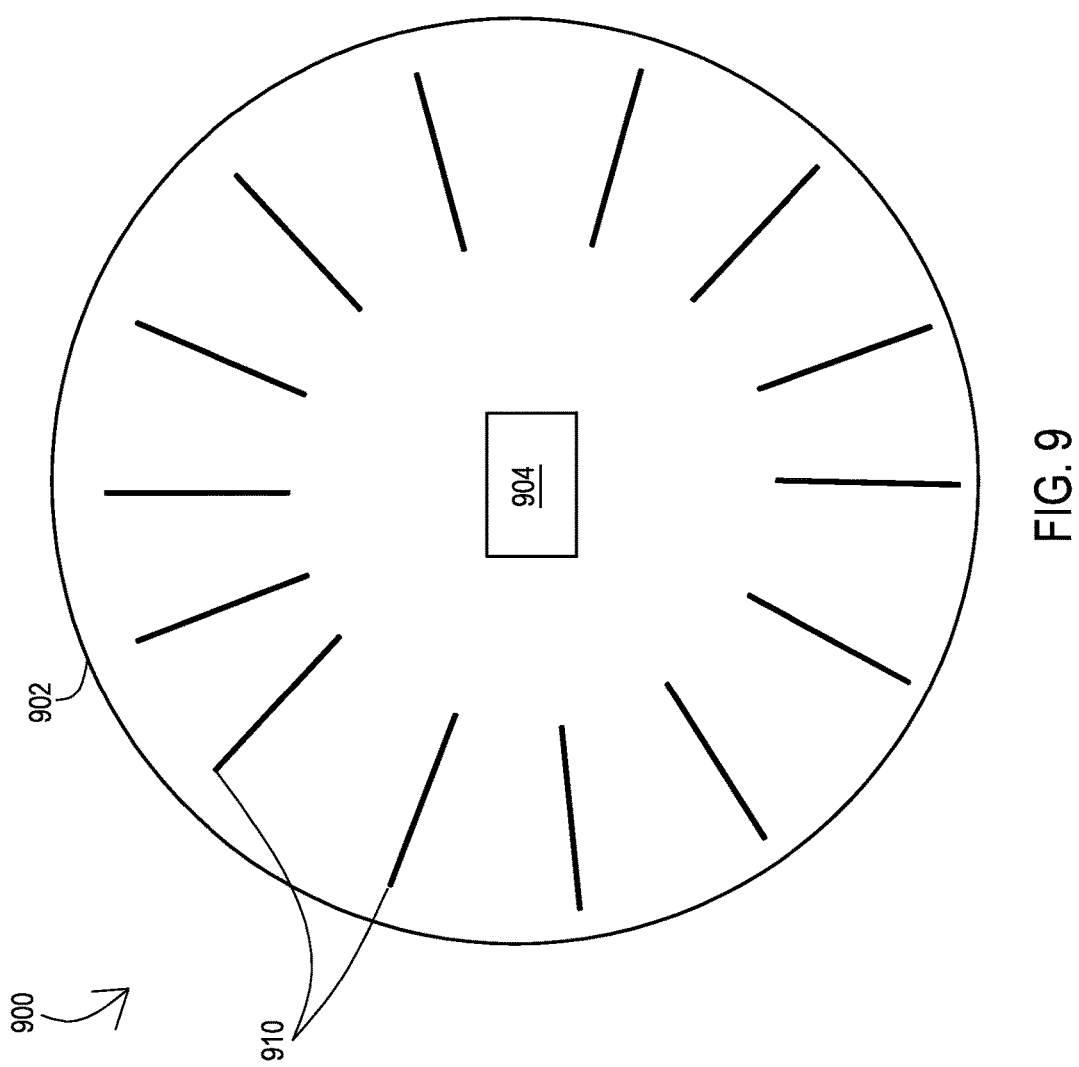
FIG. 9 illustrates a third spinning disk pattern, in accordance with one embodiment of the present invention.

FIG. 9 illustrates a third spinning disk pattern 900, in accordance with one embodiment of the present invention.

The third spinning disk pattern 900 may include a plurality of slits 910 extending from an outer edge 902 of the third spinning disk pattern 900 to a middle portion 904 of the third spinning disk pattern 900. The slits 910 form a pinwheel type of orientation on the third spinning disk pattern 900.

Figure 10:
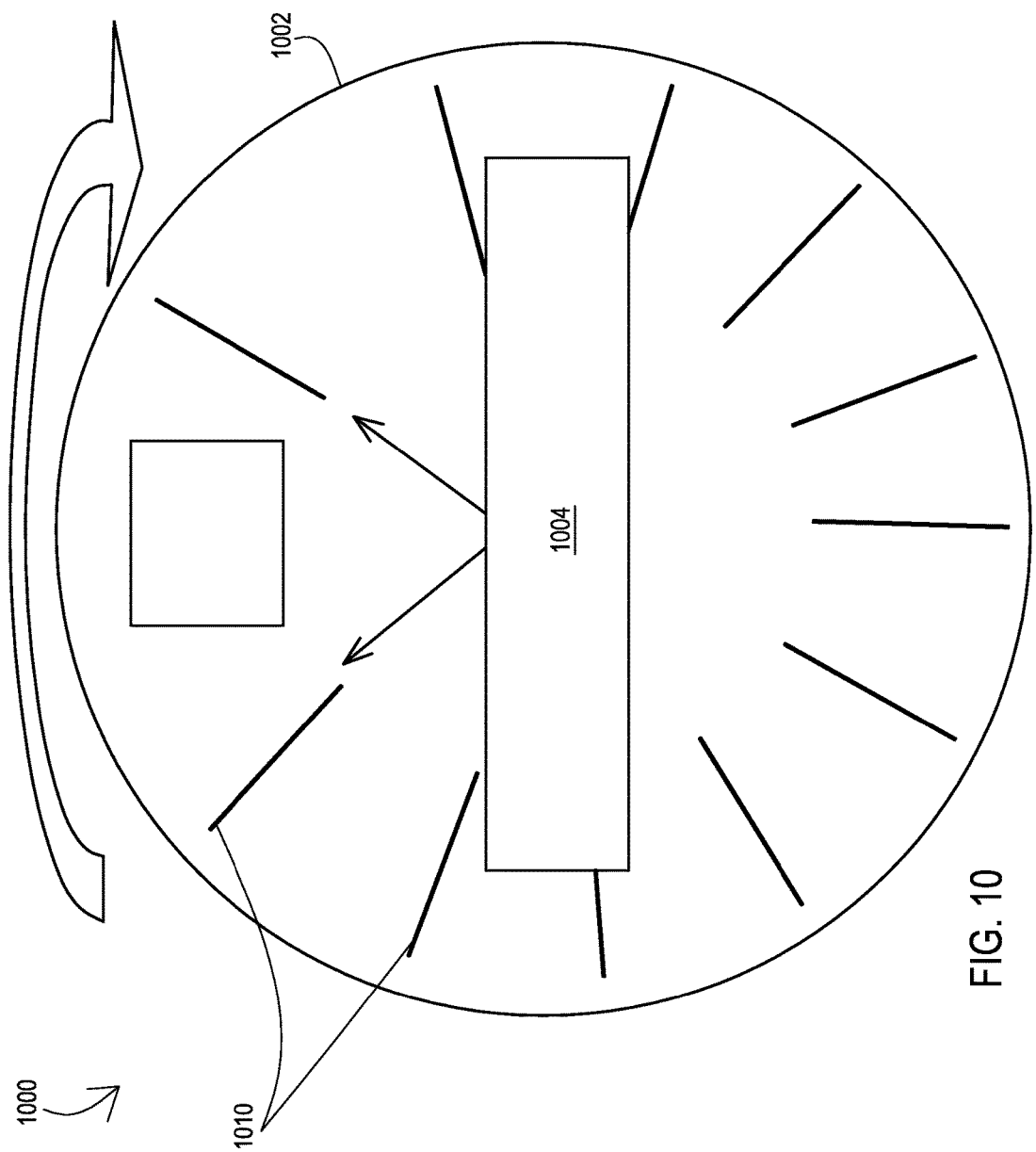
FIG. 10 illustrates a slit scanning disk pattern, in accordance with one embodiment of the present invention.

FIG. 10 illustrates a slit scanning disk pattern 1000, in accordance with one embodiment of the present invention.

The slit scanning disk pattern 1000 include a plurality of slits 1010 extending from an outer edge 1002 of the third spinning disk pattern 1000 to a middle portion 1004 of the third spinning disk pattern 1000. The slits 1010 form a pinwheel type of orientation on the third spinning disk pattern 1000. Each of the slits 1010 passes over an array at an approximate rate of one exposure time of camera.

The system and method for rejecting afocal light collected from an in vivo human retina includes several elements. These elements include a spinning disk which is a flat circular disk made of a thin aluminum sheet, or opaque material such as polyoxymethylene or DELRIN® or pigmented high-density polyethylene or HDPE or acrylonitrile butadiene styrene or ABS, or a lithographic construction of a trans missive substrate with an opaque pattern adhered to the substrate, is affixed directly to a direct current or DC motor, or affixed at its center axis to a pulley, which is then attached via a para aramid synthetic fiber or KEVLAR® belt to a DC motor, or affixed at its center axis to an involute gear, which mates to a gear of similar design which is then driven by a DC motor. In this iteration the disk may be removable, allowing a system operator to choose between the best disk shape, pinhole/slit/cut style and size for a specific application. The disk may in addition include a highly reflective coating on its sample-side, which may be utilized to reflect light onto the subject. The disk may be flat, curved in a shape similar to an umbrella, or curved into a parabolic type shape, to aid in the focusing of light onto the subject. The disk may include holes, cuts, or shapes of different sizes, dependent of the radius from the center of the disk. The disk may also integrate into its reflective coating, or as a separate layer, a polarizing layer, utilized to control what light enters the return image path of the pinholes, slits, or cuts.

In one case only a single disk may be utilized. In other cases such as structured excitation, two or more disks may be utilized. The DC motor spins at a desired revolutions per minute or RPM specified by a pulse width modulated or PWM controller. The DC motor may be shaft coupled, pulley coupled or gear coupled on its spindle. The disk has on its side an index, or fiducial, notch. This notch (or magnet or other marking) indicates the zero degree orientation of the disk. The fiducial position is scanned during disc operation continually by a high speed infrared optical interrupter or similar sensor. The interrupter serves two functions: first, it reports the zero degree position to a control board, which is utilized to drive the PWM signal to the DC motor. By sensing and recording the frequency of the fiduciary mark, the opto-interrupter is able to report the number of indications found on the wheel for a duration of time. This may then be calculated as revolutions per minute. This information is essential to generating a field coverage of dots, slits, or cuts in the disk over the array detector, without which would yield lines, shapes, or other artifacts in the acquired final image. The second function of the optical interrupter is to report zero degree position to the controller, to be utilized in synchronization with the detector. This is of specific importance in the example wherein a series of vertical or horizontal lines are utilized to slit scan the image. In this case it is essential the timing of the detector's exposure and the slit speed and position are matched. If these two systems are not matched in both speed and start position, artifacts will appear in the image such as dim areas, or saturated or bright areas, where no confocality or useful data is yielded. A light delivery system is utilized to deliver illumination to the subject. This illumination may be utilized for reflected light, or for fluorescence excitation. In the case of reflected light the source utilized may be a gas-arc lamp, wide bandwidth light-emitting diode or LED or LED engine, or other wide bandwidth illuminator. In the case of fluorescence excitation, the source utilized may include a laser, an LED, a pumped phosphor engine, an arc lamp or a plasma ball bulb. In the case of fluorescent excitation from a wide band excitation lamp, an optical window filter would be included in the light path to restrict only those wavelengths most useful to the excitation band as entering the confocal system. Other wavelengths would be absorbed by the filter and/or reflected to the source. In the case of a laser, an x/y field scanning generator may be utilized to direct beam patterns into the specimen as predefined shapes. These shapes would then be utilized for decoding a final image. In another embodiment the disk is removed, and only a coded illumination system is utilized in its place. Numerous images are acquired wherein the input light is structured with predefined shapes. As images are obtained, the input illumination shape is changed. After a number of images are obtained, software may be utilized to derive how the unknown or patient optical system is characterized. Once this characterization (or convolution or aberration value) is known, it may be removed from the image, leaving only correct signal. In another embodiment the disk is mounted in an off angle orientation to the optical centerline. In this implementation when the disk spins, numerous holes of varying sizes (focus positions relative to the back focal plane of the objective utilized) are presented to the detector. This may yield a useful measurement of optical noise, or a measurement of aberrations, or a measurement of height.

In another embodiment the spinning disk speed is adjusted during detector capture. In another embodiment the size of the pinhole in the spinning disk is adjustable dynamically. In another embodiment the device incorporates an adaptive optics subsystem to correct for optical aberrations in the eye. In another embodiment, the sensor is placed in an accumulation mode, wherein the sensor accumulates electrons in its potential well, but does not shift them beyond its parallel register. Several accumulations are collected using a high speed laser or LED pulse. This embodiment has the advantage of reducing patient discomfort by reducing the time photon correlation as related to the patient's retinal tissue, and may reduce iris constriction. In another embodiment the system may be coupled with or combined with conventional fundus cameras, or optical coherence tomography instruments. In another embodiment the system may be coupled with infrared light and utilized off-axis, to produce representations of surface objects which interact with reflected infrared illumination. In another embodiment the instrument is coupled to a high speed spectral excitation device, and numerous images are obtained while small shifts in the wavelength peak of the excitation light are made. This method may be utilized to produce a hyperspectral image.

The system and method for rejecting afocal light collected from an in vivo human retina may be utilized for retinal imaging of a human or animal subject. The system and method for rejecting afocal light collected from an in vivo human retina improvements to a mode-locked slit scanner built into a wheel may be utilized for any other traditional application wherein a confocal is employed. This includes fluorescent microscopy applications, whole animal imaging applications and field sensing of any type. The system may be utilized for wide band detection and excitation, or may be utilized with specific bands of light delivered from a laser, LED, pattern generator, holographic interference optic, gas-arc lamp or other illumination device. The system may be utilized in conjunction with array scanning CCD's, CMOS sensors or other two dimensional array detectors. The ability of the system to be coupled with a variety of illumination and detection components provides two key advantages over current devices. The system allows for use in both low cost/low performance environments, and high cost/high performance environments. The system may be coupled with a low performance illuminator, a low resolution and/or low sensitivity detector (for instance a monochrome CMOS), which would be obtainable at a low price. Another iteration of the system could include a highly specific illuminator coupled to an Electron Multiplying CCD to achieve maximum sensitivity in detection.

While the present invention has been related in terms of the foregoing embodiments, those skilled in the art will recognize that the present invention is not limited to the embodiments described. The present invention may be practiced with modification and alteration within the spirit and scope of the appended claims. Thus, the description is to be regarded as illustrative instead of restrictive on the present invention.

The invention claimed is:

1. A system to reject afocal light collected from an in vivo human retina, comprising:
   a detector to collect data representing an image;
   a server system with a processor system, a communications interface, a communications system, an input system and an output system, the server system being in communication with the detector;
   a memory system with an operating system, a communications module, a web browser module, a web server application and a rejection of collected afocal light non-transitory storage media; and
   a continuously spinning disk having an optointerruptor for detecting how fast the disk is spinning and a motor to continuously spin the disk having multiple holes of varying shapes to reject out of focus light and to image an entire field of view, wherein the motor is speed controlled via the non-transitory storage media.

2. The system to reject afocal light collected from an in vivo human retina according to claim 1, further comprising a relay lens.

3. The system to reject afocal light collected from an in vivo human retina according to claim 1, further comprising an objective lens.

4. The system to reject afocal light collected from an in vivo human retina according to claim 1, further comprising an image entry lens.

5. The system to reject afocal light collected from an in vivo human retina according to claim 1, further comprising an excitation light source.

6. The system to reject afocal light collected from an in vivo human retina according to claim 1, wherein the detector is a charge coupled device.

7. The system to reject afocal light collected from an in vivo human retina according to claim 1, wherein the detector is a complementary metal oxide semiconductor.

8. The system to reject afocal light collected from an in vivo human retina according to claim 1, wherein the disk is tilted.

9. The system to reject afocal light collected from an in vivo human retina according to claim 1, wherein the disk is vertically upright at ninety degrees.

10. The system to reject afocal light collected from an in vivo human retina according to claim 1, wherein the disk has an applied reflected coating.

11. The system to reject afocal light collected from an in vivo human retina according to claim 1, wherein the disk has a plurality of pins holes that receive and direct light.

12. The system to reject afocal light collected from an in vivo human retina according to claim 1, wherein the disk includes a plurality of cross-shaped slits.

13. The system to reject afocal light collected from an in vivo human retina according to claim 1, wherein the disk includes a plurality of perpendicular slits.

14. The system to reject afocal light collected from an in vivo human retina according to claim 1, wherein the disk includes a plurality of slits extending from an outer edge of the spinning disk to a middle portion of the spinning disk.

15. The system to reject afocal light collected from an in vivo human retina according to claim 14, wherein the slits form a pinwheel type of orientation.

16. A method for rejecting afocal light collected from an in vivo human retina, comprising the steps of: utilizing a series of optical shapes or codes, similar to other structured illumination systems; illuminating the series of optical shapes or codes several times; collecting and processing the series of optical shapes or codes; yielding measurements of optical noise and optical signal; and subtracting the noise and signal from the final image, including using a continuously spinning disk having multiple holes of varying shapes to expose the retina to light through the holes and to reject out of focus light, and for collecting light to form an image of the retina.

17. The method according to claim 16, wherein the subtracting step includes achieving a result similar to a confocal system.

18. A non-transitory computer storage media having instructions stored thereon which, when executed, execute a method comprising the steps of: utilizing a series of optical shapes or codes, similar to other structured illumination systems; illuminating the series of optical shapes or codes several times; collecting and processing the series of optical shapes or codes; yielding measurements of optical noise and optical signal; and subtracting the noise and signal from the final image, including using a continuously spinning disk having multiple holes of varying shapes to expose the retina to light through the holes and to reject out of focus light, and for collecting light to form an image of the retina.

19. The non-transitory computer storage media according to claim 18, wherein the subtracting step includes achieving a result similar to a confocal system.

20. A system to reject afocal light collected from an in vivo human retina, comprising:
   a light source;
   a continuously spinning disk having multiple holes having varying shapes to expose the retina to light through the holes and to reject out of focus light; and
   a detector for receiving light after passing through the holes and reflected off the retina and for collecting light to form an image of the retina.

21. The system of claim 20, further comprising a relay lens.

22. The system of claim 20, further comprising an objective lens.

23. The system of claim 20, further comprising an image entry lens.

24. The system of claim 20, wherein the detection is selected from the group consisting of a charge coupled device and commentary metal oxide semiconductor.

25. The system of claim 20, wherein the disk is tilted.

26. The system of claim 20, wherein the disk is vertically upright at ninety degrees.

27. The system of claim 20, wherein the disk has an applied reflected coating.

28. The system of claim 20, wherein the disk includes a plurality of cross-shaped slits.

29. The system of claim 20, wherein the disk includes a plurality of perpendicular slits.

30. The system of claim 20, wherein the disk includes a plurality of slits extending from an outer edge of the spinning disk to a middle portion of the spinning disk.

31. The system of claim 20, wherein the slits form a pinwheel type of orientation.

* * * * *